United States Patent
Inukai et al.

(10) Patent No.: US 11,065,417 B2
(45) Date of Patent: Jul. 20, 2021

(54) METHOD FOR MANUFACTURING CATHETER AND CATHETER MANUFACTURED BY THIS MANUFACTURING METHOD

(71) Applicant: TERUMO KABUSHIKI KAISHA, Tokyo (JP)

(72) Inventors: Takito Inukai, Fujinomiya (JP); Shun Matsushita, Fujinomiya (JP); Yuya Otake, Fujinomiya (JP); Kota Hamuro, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 28 days.

(21) Appl. No.: 16/279,083

(22) Filed: Feb. 19, 2019

(65) Prior Publication Data
US 2019/0255282 A1 Aug. 22, 2019

(30) Foreign Application Priority Data

Feb. 20, 2018 (JP) .............................. JP2018-028006
Sep. 26, 2018 (JP) .............................. JP2018-179812

(51) Int. Cl.
*B29C 45/14* (2006.01)
*A61M 25/00* (2006.01)
(Continued)

(52) U.S. Cl.
CPC .... *A61M 25/0014* (2013.01); *A61M 25/0023* (2013.01); *A61M 25/0097* (2013.01);
(Continued)

(58) Field of Classification Search
None
See application file for complete search history.

(56) References Cited

U.S. PATENT DOCUMENTS

| 4,284,459 A | 8/1981 | Patel et al. |
| 6,068,622 A | 5/2000 | Sater et al. |
| (Continued) | | |

FOREIGN PATENT DOCUMENTS

| EP | 0824930 A2 | 2/1998 |
| EP | 3 047 867 A1 | 7/2016 |
| (Continued) | | |

OTHER PUBLICATIONS

The extended European Search Report dated Jul. 17, 2019, by the European Patent Office in corresponding European Patent Application No. 19158020.8-1014. (12 pages).

*Primary Examiner* — Monica A Huson
(74) *Attorney, Agent, or Firm* — Buchanan Ingersoll & Rooney PC

(57) ABSTRACT

A catheter manufacturing method includes positioning a shaft in a cavity of a mold. The shaft is an elongated tubular body configured to be inserted into a living body. The mold includes a first mold die and a second mold die that contact one another to define a closed space which is the cavity. The method includes injecting a molding material into the cavity from a gate at a position between the proximal end and the distal end of the shaft in the axial direction. The injecting position is offset from the center of the shaft in the transverse direction. The method includes molding a hub onto the shaft by solidifying the injected molding material in the cavity onto the outer surface of the shaft.

8 Claims, 9 Drawing Sheets

(51) Int. Cl.
*B29C 45/26* (2006.01)
*B29C 45/00* (2006.01)
B29K 101/12 (2006.01)
B29L 31/00 (2006.01)

(52) U.S. Cl.
CPC .... *B29C 45/0025* (2013.01); *B29C 45/14598* (2013.01); *B29C 45/261* (2013.01); *A61M 25/0041* (2013.01); *A61M 2025/0008* (2013.01); *A61M 2025/0042* (2013.01); *A61M 2207/10* (2013.01); *B29C 45/0046* (2013.01); *B29C 45/14073* (2013.01); *B29C 2045/0027* (2013.01); *B29K 2101/12* (2013.01); *B29L 2031/7542* (2013.01)

(56) References Cited

U.S. PATENT DOCUMENTS

| | | |
|---|---|---|
| 6,575,959 B1 | 6/2003 | Sarge et al. |
| 2017/0151417 A1* | 6/2017 | Takemura ............... B29C 45/72 |

FOREIGN PATENT DOCUMENTS

| | | |
|---|---|---|
| JP | 10180802 A | 7/1998 |
| JP | 2001-047475 A | 2/2001 |
| JP | 2005-305868 A | 11/2005 |
| WO | 03/039639 A2 | 5/2003 |

\* cited by examiner

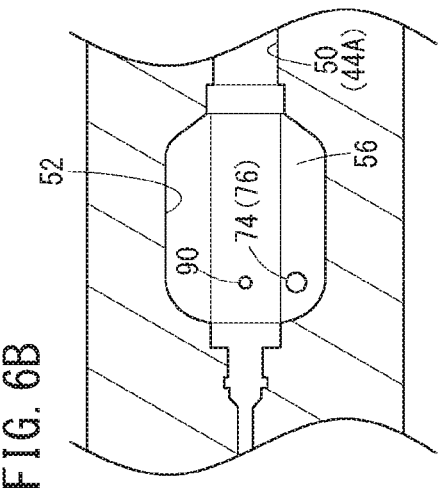
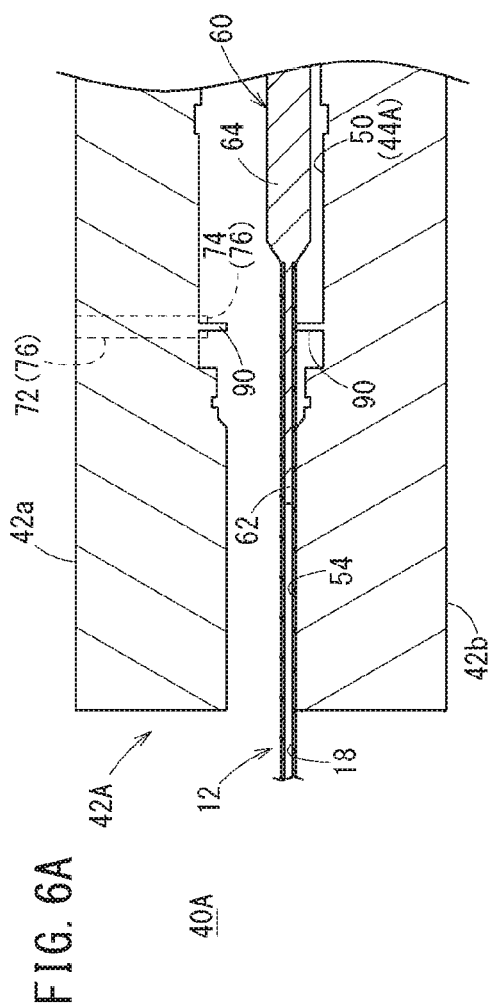
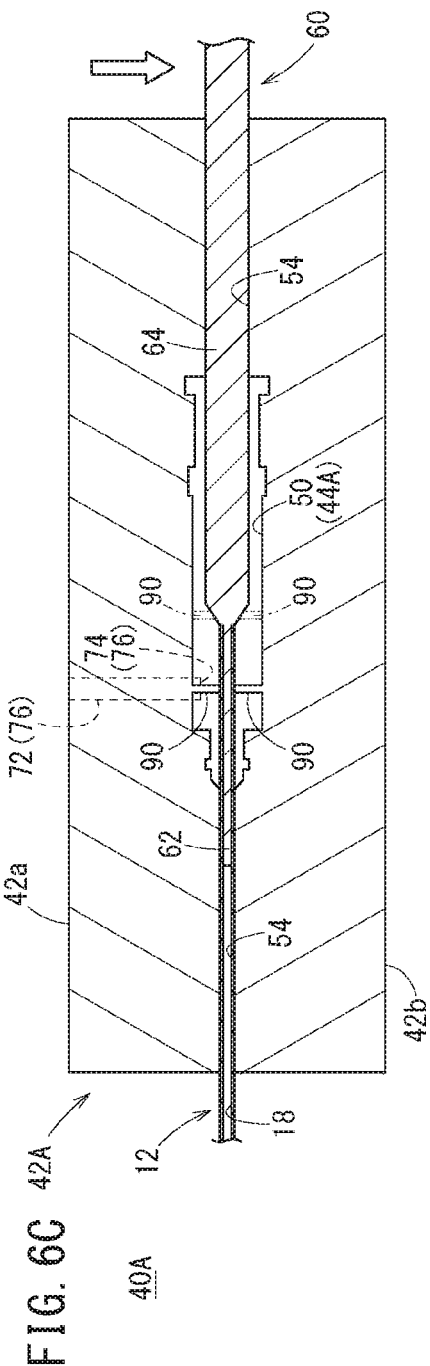

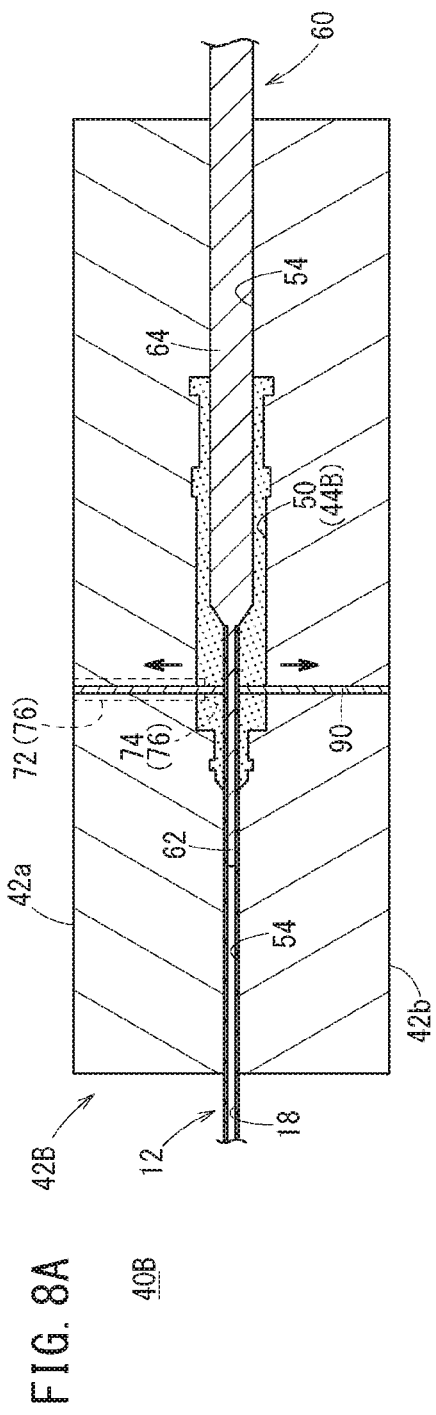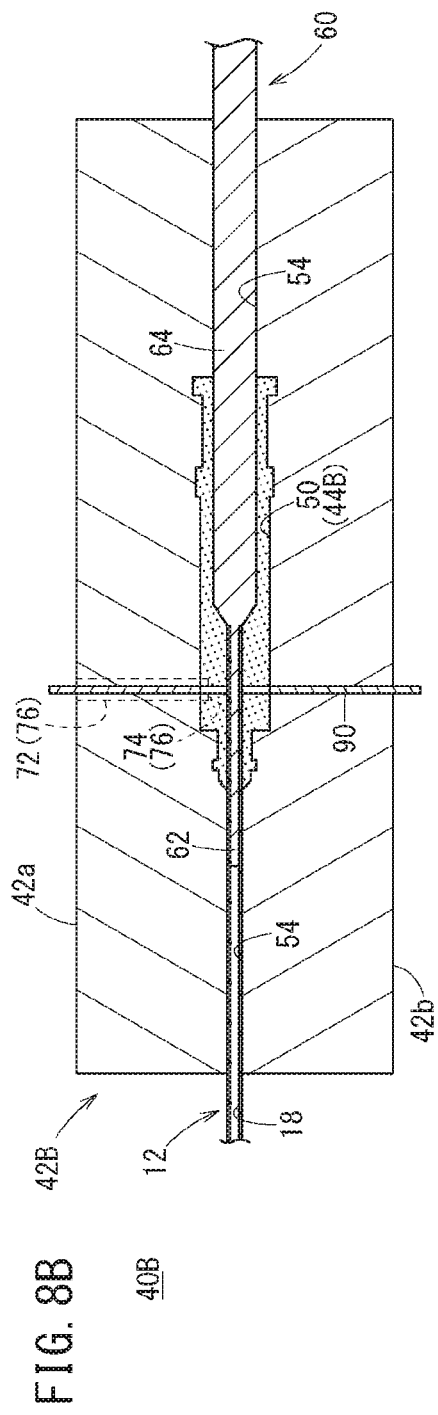

METHOD FOR MANUFACTURING CATHETER AND CATHETER MANUFACTURED BY THIS MANUFACTURING METHOD

CROSS-REFERENCES TO RELATED APPLICATIONS

This application claims priority to Japanese Application No. 2018-028006 filed on Feb. 20, 2018 and Japanese Application No. 2018-179812 on Sep. 26, 2018, the entire content of which is incorporated herein by reference.

FIELD OF THE INVENTION

The present invention generally relates to a catheter manufacturing method for insert-molding a hub on a shaft and a catheter manufactured by the manufacturing method.

BACKGROUND DISCUSSION

A catheter for medical use is provided with a flexible shaft for insertion into a patient. A hub may be provided at the proximal end of the shaft with the hub being harder (more rigid) than the shaft. In this type of catheter, the shaft and the hub are integrated by a fixing method such as adhesion, caulking, and insert molding. For example, Japanese Patent Application Publication No. 10-180802 discloses a manufacturing method for insert-molding a hub to adhere the hub to a shaft by disposing the shaft in a cavity of a mold and injecting a molding material.

SUMMARY

In the insert molding-based manufacturing method disclosed in Japanese Patent Application Publication No. 10-180802, the molding material is injected into the cavity of the mold at a high pressure and a high speed. Accordingly, there is a possibility that the shaft is deformed or the shaft moves relative to the mold depending on how/where the molding material is disposed onto (contacts) the shaft. In other words, the joining position of the shaft and the hub is likely to shift to an unintended place during the insert molding. This shift can lead to product quality deterioration by entailing, for example, a change in the axial length of the catheter as a whole.

According to the manufacturing method disclosed in Japanese Patent Application Publication No. 10-180802, a flange is provided in an end portion of the shaft and the mold is provided with a concave portion engaged with the flange so that the shaft is prevented from shifting. However, the flange formation on the shaft and flange disposition at an appropriate position of the mold result in an increase in manufacturing process complexity and an increase in cost.

The catheter manufacturing method and a catheter manufactured by the manufacturing method disclosed here may help achieve product quality enhancement by deterring a shaft movement during insert molding with a relatively simple configuration.

The disclosed catheter manufacturing method involves fixing a shaft and a tubular hub provided at a proximal end of the shaft to each other by insert molding. The method includes a disposition step for disposing the shaft in a cavity provided in a mold of a manufacturing apparatus, an injection step for injecting a molding material from a gate provided on an inner wall constituting the cavity after the disposition step, and a molding step for molding a hub adhering to the shaft by solidifying the injected molding material in the cavity. The shaft is positioned in the disposition step such that the gate is between a distal end and the proximal end of the shaft in lateral cross-sectional view of the mold parallel to an extending direction of the shaft.

The mold may include a runner that allows the molding material to flow toward the gate and the shaft may be disposed in the disposition step such that the extending direction of the shaft has a position twisted with respect to an extending direction of the runner.

The hub may have a tubular hub main body and a wing protruding from an outer peripheral surface of the hub main body, the cavity may have a first space for molding the hub main body and a second space for molding the wing, and the shaft may be disposed along an axis of the first space in the disposition step.

In addition to the above configuration, it is preferable that the extending direction of the runner intersects with the second space.

Here, the method may include a mold clamping step for clamping the mold after the disposition step and before the injection step. The shaft may be pressed by at least one pin provided in the mold in a state where the mold is clamped in the mold clamping step.

Preferably, a concave portion is formed in the hub by the pin in the injection step and the molding step.

A plurality of the pins may be arranged side by side along an axial direction of the shaft disposed in the disposition step.

The method may include a mold opening step for opening the mold after the molding step and a withdrawal step for withdrawing the pin from the cavity between the molding step and the mold opening step.

The disclosed catheter includes a shaft and a tubular hub fixed by insert molding to a proximal end of the shaft. The hub has residual stress at the casting wall of the hub and the residual stress at a predetermined position between a distal end and the proximal end of the shaft exceeds the residual stress at a position shifted in an axial direction of the hub from the predetermined position.

In another embodiment, the disclosed catheter includes an elongated shaft extending in a longitudinal direction and possessing an outer surface, the shaft possessing a distal end, a proximal end and a proximal portion which includes the proximal end, a transverse direction being perpendicular to the longitudinal direction. The catheter includes a tubular hub fixed by insert molding to the outer surface of the shaft along the proximal portion of the shaft. The hub possesses a residual stress at one predetermined location of the hub that exceeds the residual stress of the hub at each of: (i) a first position distal to the one predetermined location, (ii) a second position proximal to the one predetermined location, and (iii) a third position being at the one predetermined location in the longitudinal direction and spaced apart from the one predetermined location in the transverse direction.

In yet another embodiment, a catheter is disclosed that includes an elongated shaft extending in a longitudinal direction and possessing an outer surface, the shaft possessing a distal end, a proximal end and a proximal portion which includes the proximal end, a transverse direction being perpendicular to the longitudinal direction. The catheter includes a tubular hub fixed by insert molding to the outer surface of the shaft along the proximal portion of the shaft. The tubular hub includes a tubular hub main body and a pair of wings protruding from the hub main body outward in the transverse direction. The hub has a first residual stress state and a second residual stress state different from the first residual stress state. The first residual stress state in one of the pair of wings at a predetermined position and the second residual stress state is in the other of the pair of wings opposite to the predetermined position in the transverse direction.

Specifically, the second shape may have a gate trace formed during injection molding of the hub and protruding from a surface.

The hub may have a tubular hub main body and a pair of wings protruding from an outer peripheral surface of the hub main body and the pair of wings may differ from each other in terms of the residual stress in cross-sectional view orthogonal to the axial direction of the hub at the predetermined position.

The shaft may be curved in one direction between the distal end and the proximal end, the hub may have a tubular hub main body and a pair of wings protruding from an outer peripheral surface of the hub main body, and at least one of the wings may be provided with a marker indicating a curvature direction of the shaft.

In this case, the marker may be disposed on the same side as an outside of curvature of the shaft with respect to a central axis of the shaft.

Alternatively, the marker may be disposed on the same side as an inside of curvature of the shaft with respect to a central axis of the shaft.

The catheter manufacturing method disclosed here helps to deter (prevent) the shaft from moving during insert molding by positioning the shaft such that the gate is between the distal end and the proximal end of the shaft in the disposition step. In other words, although the molding material is injected from the gate and reaches a high pressure during molding material injection, the injected molding material actively flows in the proximal direction from the gate. Accordingly, the force pushing the shaft distally (in the distal direction) is significantly reduced, and the hub can be molded with the shaft maintained at a predetermined position in the cavity. As a result, the quality of the catheter manufactured by this manufacturing method is significantly enhanced, and manufacturing yield improvement and the like can be achieved.

In the hub of the disclosed catheter, a large residual stress is generated at the casting wall of the place where the gate was present during the insert molding. In other words, it can be said that the gate was positioned between the distal end and the proximal end of the shaft when the residual stress at a predetermined position between the distal end and the proximal end of the shaft exceeds the residual stress at a position shifted in the axial direction of the hub from the predetermined position. Accordingly, the catheter has high quality as a movement of the shaft is inhibited during the insertion molding and the hub is tightly fixed.

BRIEF DESCRIPTION OF DRAWINGS

FIG. 6A is a lateral cross-sectional view illustrating a mold of a catheter manufacturing apparatus according to a second embodiment.

FIG. 6B is a plan view illustrating the positions of a gate and a pin of a first molding die.

FIG. 6C is a lateral cross-sectional view illustrating a state where the mold in FIG. 6A is clamped.

FIG. 8A is a lateral cross-sectional view illustrating a mold of a catheter manufacturing apparatus according to a modification example.

FIG. 8B is a lateral cross-sectional view illustrating an operation of the manufacturing apparatus in FIG. 8A.

DESCRIPTION OF EMBODIMENTS

Figure 1A:
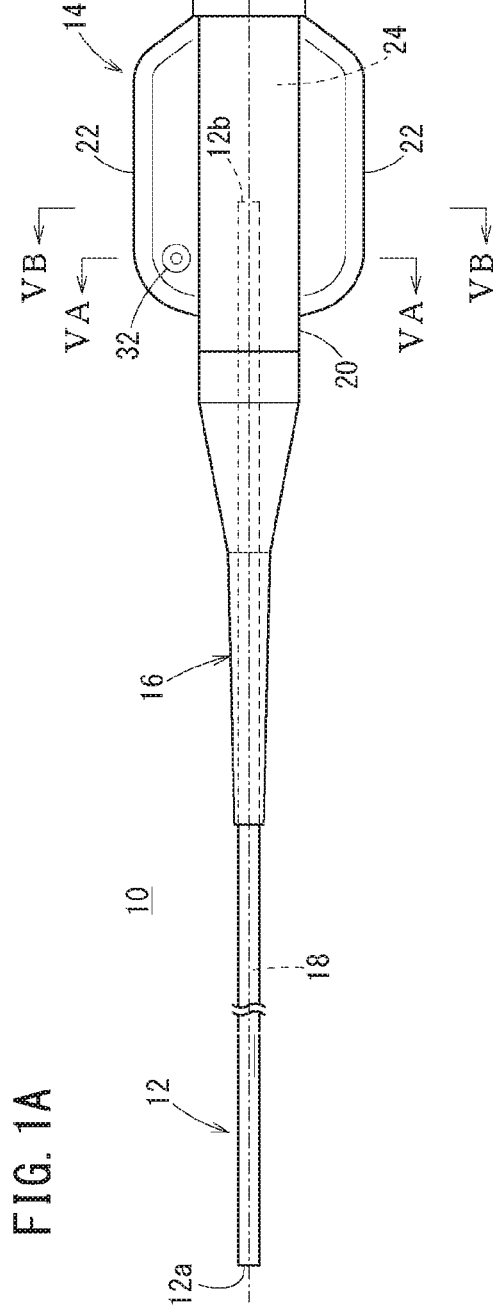
FIG. 1A is a partial plan view illustrating the proximal side of a catheter according to a first embodiment.

Set forth below with reference to the accompanying drawings is a detailed description of embodiments of a method of manufacturing a catheter and a catheter manufactured by the method representing examples of the disclosed here. Note that the description below does not restrict the technical scope or the meaning of a term described in claims. In addition, a ratio of dimensions in the drawings is exaggerated for convenience and may be different from an actual ratio.

First Embodiment

A catheter according to a first embodiment is a medical instrument for intervention that is inserted into a patient's body lumen (such as his or her blood vessel, bile duct, trachea, esophagus, urethra, nasal cavity, and another organ). In the following description, the configuration of the catheter will be described first and a method for manufacturing the catheter will be described next so that the disclosed manufacturing method and manufactured catheter can be easily understood.

Figure 1B:
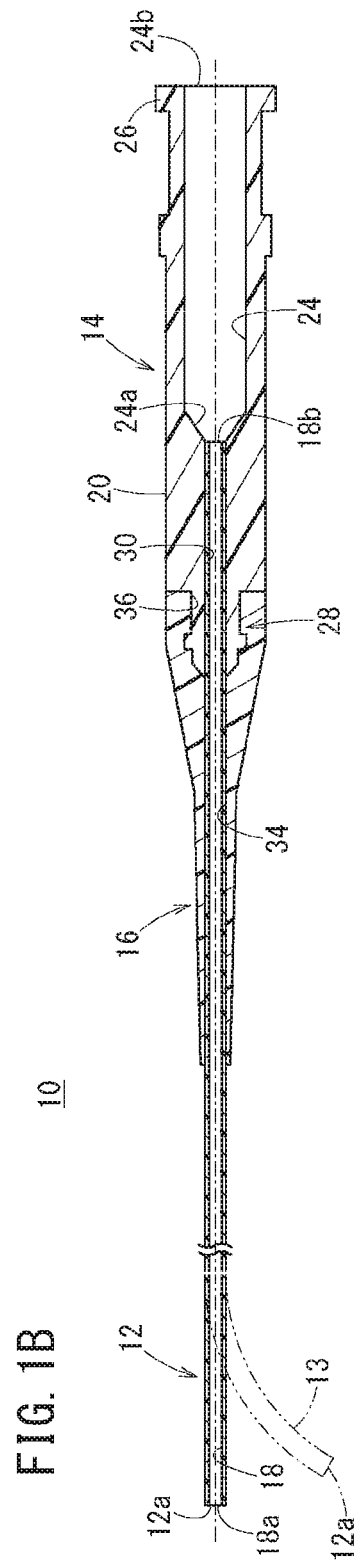
FIG. 1B is a lateral cross-sectional view of the catheter shown in FIG. 1A.

The catheter 10 includes a flexible shaft 12, a hub 14 provided at one end (proximal end) of the shaft 12, and a strain relief 16 provided at the distal end of the hub 14 as illustrated in FIGS. 1A and 1B. The hub 14 is harder (more rigid) than the shaft 12. The shaft 12 and the hub 14 are insert-molded by the manufacturing method according to the present embodiment and integrated with each other (i.e., joined to one another to move together as an integral structure).

The shaft 12 of the catheter 10 is formed in an elongated pipe body (i.e., a tubular or cylindrical body) having a distal end 12a and a proximal end 12b. The shaft 12 is inserted into a body lumen from the outside of the patient by the operation of a user such as a surgeon. A lumen 18 is formed inside the shaft 12 along the axial direction of the shaft 12. The lumen 18 communicates with each of a distal opening 18a (i.e., an open distal end) provided at the distal end 12a of the shaft 12 and a proximal opening 18b (i.e., an open proximal end) provided at the proximal end of the shaft 12. During patient treatment, for example, the lumen 18 allows medicine supplied from the proximal opening 18b to flow in the distal direction and allows the medicine to flow out of the distal opening 18a.

It is preferable that the shaft 12 of the catheter 10 is formed to have an axial length corresponding to the body type of the patient, the treatment target site or the test target of the body lumen, and the like. Although not particularly limited, the axial length of the shaft 12 is, for example, 300 mm to 3,000 mm. Preferably, the length is 1,200 mm to 2,800 mm. More preferably, the length is approximately 1,500 mm to 2,400 mm.

The shaft 12 extends with a substantially constant thickness along the axial direction. The outer diameter of the shaft 12 is not particularly limited, and the shaft 12 may be formed to have a thickness that allows insertion into a target body lumen. For example, the outer diameter of the shaft 12 is 0.5 mm to 3.0 mm. Preferably, the outer diameter is 1.0 mm to 2.8 mm. More preferably, the outer diameter is approximately 2.3 mm to 2.6 mm. The inner diameter of the shaft 12 may be designed to have an appropriate dimension in accordance with the outer diameter of the shaft 12. For example, the inner diameter of the shaft 12 may be 0.2 mm to 2.8 mm. Preferably, the outer diameter is 0.8 mm to 2.6 mm. More preferably, the outer diameter is set to approximately 2.1 mm to 2.4 mm.

It should be noted that the outer diameter and the inner diameter of the shaft 12 may be changed along the axial direction (i.e., the outer and/or inner diameter of the shaft 12 may vary along the axial direction such that the outer and/or inner diameters are non-constant throughout the length of the shaft 12). For example, the catheter 10 in which a hollow portion 24 of the hub 14 communicates with the lumen 18 of the shaft 12 may have a shaft slope having an inner diameter increasing toward the proximal direction on the inner peripheral surface of the proximal portion of the shaft 12, so as to have an angle with respect to the central axis of the catheter 10. In this configuration, the inner surface of the hub 14 constituting the hollow portion 24 may be provided with a hub slope continuing from the shaft slope at the same tilt angle as the angle that the shaft slope forms with respect to the central axis. Then, a treatment device with a large outer diameter can be relatively easily inserted or delivered with respect to the shaft 12.

Alternatively, the proximal portion of the shaft 12 may be configured to have a relatively large angle with respect to the central axis of the catheter 10 and be embedded in the inner surface of the hub 14. In this case, the resin of the hub 14 is capable of flowing into the inner surface of the shaft 12 and partially covering the proximal portion of the inner layer of the shaft 12. The resin of the hub 14 may flow into a site that is parallel to the central axis, may cover a part of the shaft slope, or may cover only the shaft proximal cross section. Further, each of the shaft slope and the hub slope may be the same or different with respect to the central axis of the catheter 10.

The shaft 12 may be comprised of an outer layer, an intermediate layer made of a metal material-based reinforcement body, and an inner layer with respective end portions that may coincide in the proximal portion or spread such that the reinforcement body expands in outer diameter with the outer layer removed in part (i.e., a proximal portion of the reinforcement body may not be covered by the outer layer). Then, the adhesion between the proximal portion of the shaft 12 and the hub 14 is improved.

The shaft 12 material is not particularly limited. Examples of the shaft 12 material include polyolefin-based resin such as high-density polyethylene, polypropylene, polybutene, polyvinyl chloride, and ethylene-vinyl acetate copolymer, polyolefin-based elastomer thereof, fluorine-based resin, fluorine-based elastomer, methacrylic resin, polyphenylene oxide, modified polyphenylene ether, polyethylene terephthalate, polybutylene terephthalate, polyether ether ketone, polyamide imide, polyether imide, polyether sulfone, cyclic polyolefin, polyurethane-based elastomer, polyester-based elastomer, polyamide, polyamide-based elastomer, polycarbonate, polyacetal, styrene-based resin, styrene-based elastomer, and thermoplastic polyimide. The shaft 12 may be comprised of a plurality of layers. For example, the shaft 12 may have an inner layer and an outer layer made of different resin materials. An intermediate layer such as a braid made of a metal material may be provided between the inner and outer layers.

The hub 14 of the catheter 10 functions as a connector for connection between the catheter 10 and another medical instrument (such as another catheter or a syringe) or a grasping unit for a user to maneuver (i.e., operate or grasp) when using the catheter 10. Accordingly, the hub 14 is formed to be harder (more rigid) than the shaft 12 as described above and is formed to be thicker than the shaft 12.

The hub 14 according to the present embodiment has a hub main body 20 fixed to the shaft 12 and a pair of wings 22 provided on the outer peripheral surface of the hub main body 20.

The hub main body 20 is formed in a cylindrical shape having the hollow portion 24 therein. A flange 26 is provided on the proximal side outer peripheral surface of the hub main body 20. The flange 26 protrudes radially outwards from the hub main body 20 and is ring shaped (i.e., possesses a circular cross section). The flange 26 may conform to a standard allowing connection of various medical instruments. A screw thread is formed in the outer peripheral portion (i.e., in the outer surface) of the flange 26.

A mounted portion 28 for mounting and holding the strain relief 16 is provided in the distal portion of the hub main body 20. A projection for connecting the strain relief 16 to the hub main body 20 may be provided on a circumferential part or the outer periphery (outer surface) of the mounted portion 28. It should be noted that the hub 14 may be configured to allow replacement the strain relief 16 by the distal portion of the hub main body 20 becoming gradually flexible.

The distal side of the inside of the hub main body 20 (including the mounted portion 28) is a fixed portion 30 for adhesion and fixing of the proximal side part of the shaft 12 (i.e., the distal part of the radially inward surface of the hub main body 20 is fixed/adhered to the proximal part of the outer surface of the shaft 12). The fixed portion 30 is a part that extends by a predetermined length along the axial direction of the hub main body 20 and firmly adheres to the shaft 12 by insert-molding. The hollow portion 24 of the hub main body 20 is provided on the proximal side of (proximal to) the fixed portion 30 and extends along the axial direction of the hub main body 20. The distal part of the hollow portion 24 is a tapered portion 24a and communicates with the proximal opening 18b of the shaft 12 fixed to the fixed portion 30 as shown in FIG. 1B. The proximal end of the hollow portion 24 is an opening portion 24b (i.e., an open proximal end) of the hub main body 20 as shown in FIG. 1B. Accordingly, the hub 14 causes (i.e., directs or allows) a liquid flowing in via the opening portion 24b to flow to the proximal opening 18b of the shaft 12.

The pair of wings 22 of the hub 14 are integrally formed with the outer peripheral surface of the hub main body 20.

The pair of wings 22 are disposed at opposite positions across the axial center of the hub 14 (positions shifted by 180° in phase). Each wing 22 protrudes radially outward of the hub main body 20 and is formed in a plate shape extending along the axial direction of the hub main body 20. The hub main body 20 may be provided with one wing 22 or three or more wings 22 instead of the pair of wings 22 shown in FIG. 1A. In addition, the hub 14 may be configured to be devoid of having any wings 22 (i.e., the wing(s) 22 may be omitted).

A gate trace 32 indicating the position of a gate 74 of a mold 42 at a time when the hub 14 is injection-molded is formed at a predetermined position (on a flat surface) of one wing 22. The gate trace 32 protrudes outward slightly from the surface of the wing 22 and does not affect the operation of the hub 14 by the user. This gate trace 32 is provided near the distal end of the wing 22 during the manufacture of the catheter 10, which is described below. It should be noted that the gate trace 32 of the hub 14 may be erased by appropriate processing such as polishing so as not to be recognized by the user.

The material that constitutes the hub 14 is not particularly limited insofar as the material is able to be molded with sufficient accuracy by injection molding. For example, a thermoplastic resin such as polypropylene, polycarbonate, polyamide, polysulfone, polyarylate, and methacrylate-butylene-styrene copolymer may be used as the hub 14 material.

The strain relief 16 is provided to inhibit a kink phenomenon in which the shaft 12 is bent as a result of stress concentration on the part where the shaft 12 and the hub 14 are connected to each other. The strain relief 16 is formed in a conical shape gradually decreasing (tapering) in outer diameter toward the distal side from the proximal end. The strain relief 16 is fixed to the mounted portion 28 and has an insertion portion 34 therein (i.e., the insertion portion 34 is a lumen or open thru-hole of the strain relief 16 as shown in FIG. 1B). The insertion portion 34 is a space through which the shaft 12 is inserted. A projection portion 36 connectable to the mounted portion 28 of the hub main body 20 is formed at the proximal end of the inner surface constituting the insertion portion 34. The strain relief 16 is made of an elastic material such as elastomer and silicone resin. In some embodiments, the catheter 10 may lack (not be provided with) the strain relief 16.

Figure 2A:
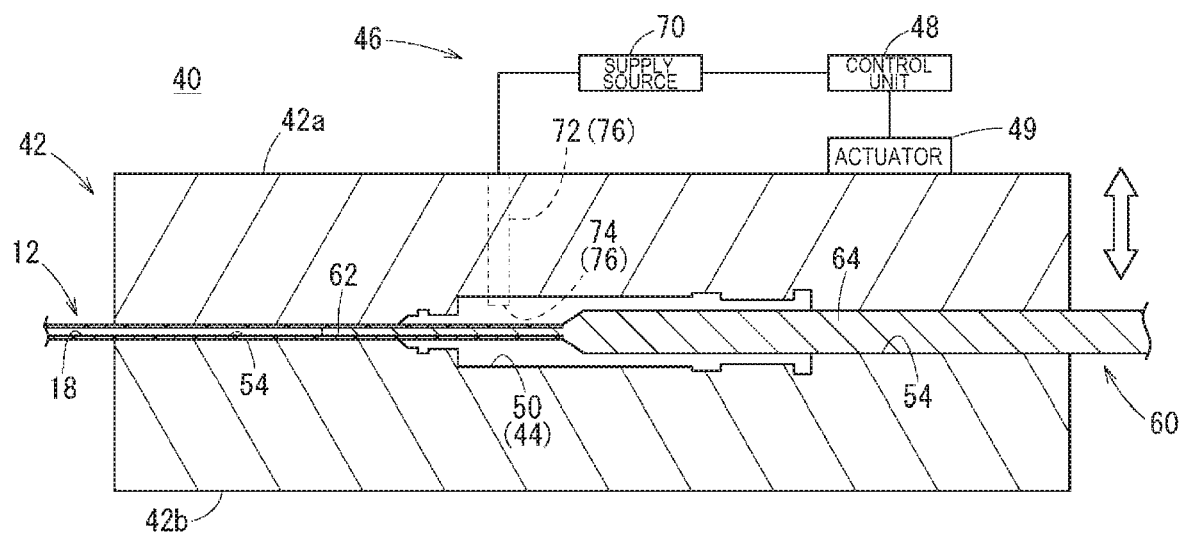
FIG. 2A is a lateral cross-sectional view illustrating a catheter manufacturing apparatus.

When the catheter 10 described above is manufactured, the molding material of the hub 14 is injected into the mold 42 in a state where the (previously molded) shaft 12 is disposed (positioned) in the mold 42. Then, the shaft 12 and the hub 14 are joined by insert molding. Next, a manufacturing apparatus 40 (injection molding apparatus) for the insert molding will be described with reference to FIGS. 2A and 2B.

The manufacturing apparatus 40 has the mold 42 having therein a cavity 44 for molding of the hub 14, an injection unit 46 supplying a molten material to the cavity 44, and a control unit 48 controlling the operations of the mold 42 and the injection unit 46. The control unit 48 is constituted by a known computer that has, for example, a processor, a memory, and an input-output interface.

The mold 42 has a plurality of molding dies (such as a first molding die 42a and a second molding die 42b). The mold 42 is connected via an actuator 49 such that the operation of the mold 42 can be controlled by the control unit 48. The control unit 48 performs mold clamping by one or both of the first and second molding dies 42a and 42b approaching and coming into contact with the other or one another. In a mold-clamped state (i.e., with the molding dies 42a, 42b contacting one another and being clamped shut), the control unit 48 causes the injection unit 46 to inject the molten material into the cavity 44 in the mold 42. Subsequently, the hub 14 is molded as a result of coagulation of the molten material. The first and second molding dies 42a and 42b are then separated from one another (i.e., moved relative to each other to open the mold 42) to expose the cavity 44, and then the molded catheter 10 is taken out.

The cavity 44 in the mold-clamped state has a first space 50 for molding of the hub main body 20 and a second space 52 for molding of the pair of wings 22. The second space 52 is continuous with the first space 50. For example, the first space 50 and the second space 52 are formed half and half in the first and second molding dies 42a and 42b (e.g., half of the first space 50 is defined by a recessed portion of the first molding die 42a and half of the first space is defined by a recessed portion of the second molding die 42b). It should be noted that the second space 52 may not be provided in a case where the hub 14 is desired to be formed without any wings 22. In addition, a part of the first space 50 may be formed in a slope shape such that the width decreases from the proximal side to the distal side.

A disposition portion 54 allowing disposition of the shaft 12 and a support rod 60 supporting the shaft 12 is formed in the contact surfaces of the first and second molding dies 42a and 42b. The disposition portion 54 is a groove that is semicircular in cross-sectional view (i.e., possesses a semicircular cross-section) and is provided in each of the first and second molding dies 42a and 42b. The grooves are joined together in the mold-clamped state, and then the shaft 12 and the support rod 60 are fixed.

The support rod 60 is a hard and linearly extending solid (i.e., non-hollow) member that has an insertion portion 62 inserted into the lumen 18 of the shaft 12 on the distal side and a core portion 64 connected to the proximal end of the insertion portion 62 and disposed in the first space 50. The outer diameter of the insertion portion 62 coincides with, is slightly larger than, or is smaller than the diameter of the lumen 18. The insertion portion 62 supports the shaft 12 with an appropriate engagement force in a state where the shaft 12 is inserted onto the support rod 60. The core portion 64 constitutes a part forming the hollow portion 24 of the hub 14 in cooperation with the mold 42. The core portion 64 is thicker (has a greater outer diameter) than the insertion portion 62. The core portion 64 is connected to the insertion portion 62 via a tapered distal part (i.e., the outer diameter gradually decreases towards the distal end).

The support rod 60 may be made of the same metal material as the mold 42. In the mold-clamped state (i.e., when the first and second mold dies 42a, 42b contact one another to create the closed cavity 44), the support rod 60 is disposed in the disposition portion 54 of the mold 42 together with the shaft 12. As a result, the parts therebetween (the insertion portion 62 and the core portion 64) are positioned so as to bridge the axial center of the cavity 44. The axial center may be disposed to be biased toward either the first molding die 42a or the second molding die 42b.

The injection unit 46 has a supply source 70 that stores or generates the molten material and supplies the molten material with an appropriate flow force. The injection unit 46 also includes a runner 72 provided in the mold 42 that directs the molten material supplied from the supply source 70 to flow into the cavity 44 of the mold 42. The injection unit 46 includes a gate 74 that allows the runner 72 and the cavity 44 to communicate with each other. For example, the runner 72 extends to the cavity 44 from the outer surface of the first molding die 42a and the gate 74 is provided at the boundary between the cavity 44 and the runner 72 (i.e., at the distal open end of the runner 72). Hereinafter, the runner 72 and the gate 74 are collectively referred to as a flowing portion 76.

Figure 2B:
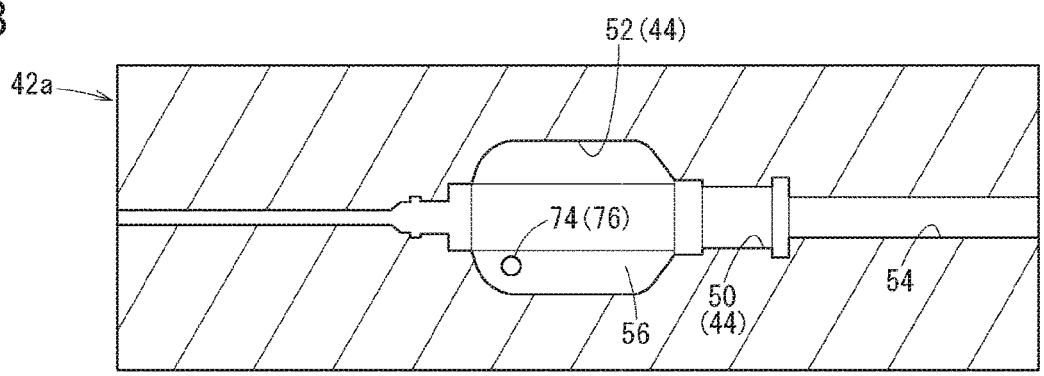
FIG. 2B is a plan view illustrating a first molding die from a partition surface.

In the present embodiment, the gate 74 is provided at a position facing the second space 52 of the first molding die 42a. Specifically, the gate 74 is disposed in a planar portion 56 facing the partition surface of the mold 42 surrounding the second space 52 as shown in FIG. 2B.

When the side of the mold 42 where the shaft 12 is disposed is defined as the distal side and the side where the core portion 64 of the support rod 60 is disposed is defined as the proximal side, the gate 74 is provided closer to the distal side than the proximal end 12b of the shaft 12 disposed in the cavity 44. In other words, the gate 74 is distal to the proximal end 12b of the shaft 12. For example, the gate 74 is positioned in the distal side range by a margin of 0.5 mm to 10 mm, more preferably approximately 1 mm to 6 mm, as compared with the proximal end 12b of the shaft 12. In other words, the gate 74 is disposed between the distal end 12a and the proximal end 12b of the shaft 12 when viewed on the axis of the shaft 12.

Figure 3:
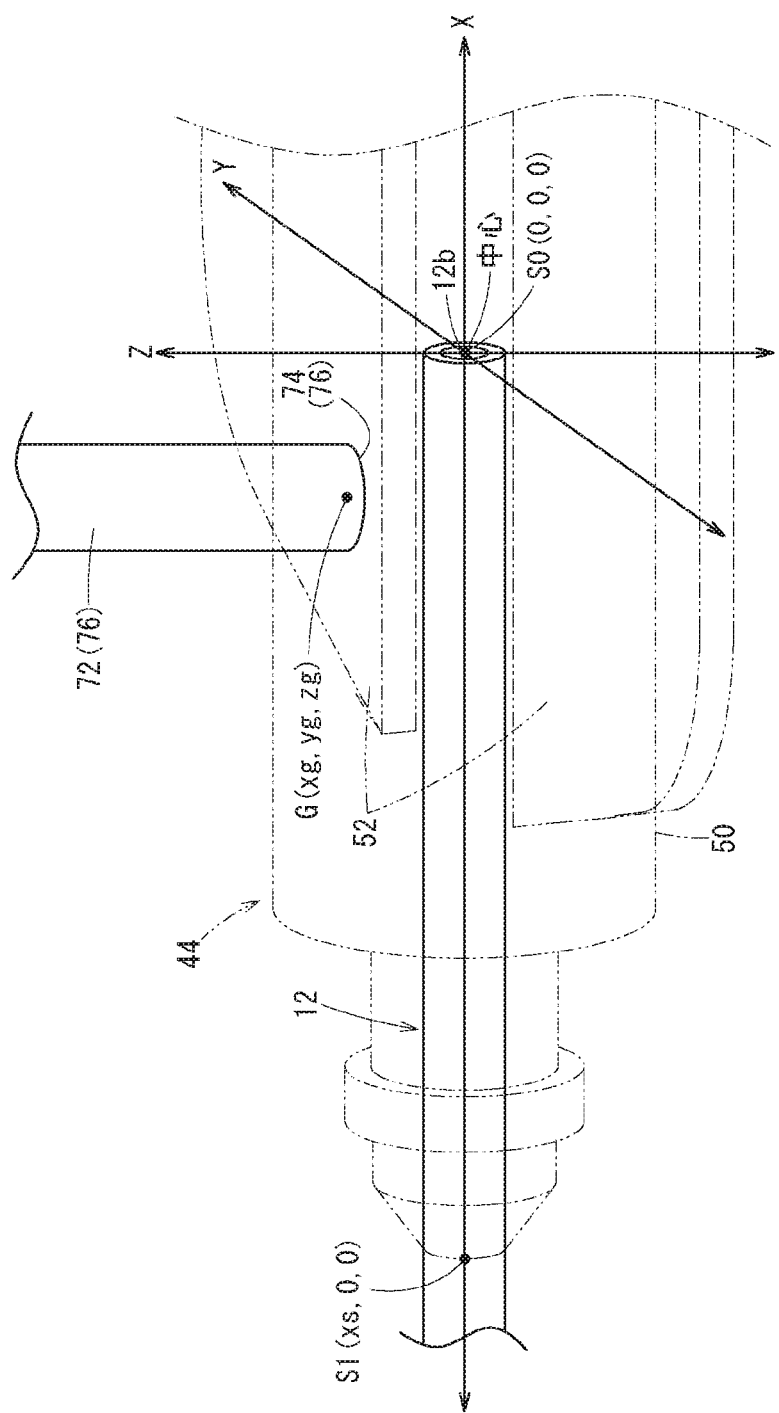
FIG. 3 is a three-dimensional coordinate diagram illustrating a gate disposition position with respect to a shaft.

The positional relationship between the shaft 12 and the flowing portion 76 (the runner 72 and the gate 74) will be described with reference to the three-dimensional coordinate diagram in FIG. 3. During the insert molding, the shaft 12 is disposed along the X axis direction of FIG. 3. In this case, the center of the proximal end 12b of the shaft 12 may be defined as being at the position of three-dimensional coordinates $S0=(0, 0, 0)$. The distal position of the hub 14 joined to the shaft 12 may thus be defined as being at the position of three-dimensional coordinates $S1=(xs, 0, 0)$. In other words, the range from 0 to xs on the X axis is the part (i.e., longitudinal extent) where the hub 14 is joined with respect to the shaft 12.

The center of the gate 74 provided in the mold 42 with respect to the extending direction (i.e., axial direction) of the shaft 12 is positioned at three-dimensional coordinates $G=(xg, yg, zg)$. The coordinate point xg on the X axis is positioned within the range of 0 to xs, and the coordinate point yg on the Y axis and the coordinate point zg on the Z axis have non-zero positions (that is, $(yg, zg) \neq (0, 0)$). In other words, the gate 74 is disposed at a position offset in the Y axis direction and the Z axis direction from the X axis where the shaft 12 is present. The coordinate point zg of the gate 74 on the Z axis is not particularly limited and zg may be zero as long as the coordinate point yg on the Y axis is not zero.

The runner 72 connected to the gate 74 is provided in the mold 42 so as to extend along the Z axis direction. In other words, the shaft 12 and the runner 72 are at positions separated from each other with mutual extending directions that are askew (i.e., the axes of the shaft 12 and the runner 72 are skew lines relative to one other) in side view (e.g., the shaft 12 extends along an axis (X axis) that is different from the axis (Z axis) of the runner 72). The extending part of the flowing portion 76 is at a non-contact and twisted position with respect to the extending part of the shaft 12. As described above, the molten material (used as the molding material to form the hub 14) is discharged into the cavity 44. As a result of this configuration of the flowing portion 76 relative to the shaft 12, the shaft 12 is absent in the injection direction of the molten material when the molten material is injected. The molten material injected from the gate 74 thus diffuses into the cavity 44 and flows towards the shaft 12 after first hitting (contacting) the inner wall constituting the cavity 44. As a result, melting of the shaft 12 by the molten material is inhibited. As illustrated in FIG. 3, in particular, the shaft 12 and the runner 72 according to the present embodiment are at positions separated from each other and have extending directions orthogonal to each other in side view. It should be noted that the partition surface of the mold 42 not only is in the X-Y plane in FIG. 3 but also can be designed in any direction within the three-dimensional (XYZ) space in FIG. 3 within a range not disturbing mold clamping or mold opening. In other words, the partition surface and the flowing portion 76 may not be orthogonal to each other.

The catheter 10 and the manufacturing apparatus 40 for the catheter 10 according to the present embodiment are configured as generally described above. The method for manufacturing the catheter 10 will be described below.

When the catheter 10 according to the present embodiment is manufactured, the hub 14 is insert-molded onto to the shaft 12. Accordingly, in the manufacturing method, a shaft providing step for obtaining the shaft 12 is performed first (Step S1). For example, the shaft 12 that is continuous in a tubular shape may be formed by means of a known shaft forming apparatus or the like. Alternatively, a shaft 12 that is separately provided may be used.

A disposition step is performed (Step S2) after the shaft providing step. In the disposition step, the insertion portion 62 of the support rod 60 is inserted into the lumen 18 of the provided shaft 12, and the shaft 12 and the support rod 60 are positioned in the disposition portion 54 of the mold 42 (e.g., in the second molding die 42b) of the manufacturing apparatus 40. As a result, the shaft 12 and the support rod 60 are disposed so as to extend along the partition surface (i.e., the upper surface) of the second molding die 42b (axial center of the cavity 44).

In the disposition step, the disposition portion 54 of the second molding die 42b allows the proximal end 12b of the shaft 12 to be positioned closer to the proximal side than the gate 74 of the mold 42 in lateral cross-sectional view of the shaft 12 and the hub 14. In other words, the gate 74 is positioned between the distal end 12a and the proximal end 12b of the shaft 12 and thus distal to the proximal end 12b of the shaft 12, and the extending direction of the shaft 12 and the extending direction of the flowing portion 76 are disposed at mutually twisted (i.e., askew) positions.

After the disposition step, mold clamping is performed on the mold 42 (mold clamping step: Step S3) by the first molding die 42a being moved relative to the second molding die 42b (in this example, where the shaft 12 and the support rod 60 are disposed). The shaft 12 and the support rod 60 are fixed (clamped) within the mold 42 as a result of this mold clamping step.

An injection step is performed (Step S4) after the mold clamping step is completed. In the injection step, the injection unit 46 is operated so that the molten material is injected through the runner 72 and out from the gate 74 into the cavity 44. As illustrated in FIG. 3, the gate 74 faces (i.e., opens into) the second space 52. The molten material flowing into the cavity 44 thus hits the inner wall of the mold 42 constituting the second space 52 and diffuses into the cavity 44. Accordingly, the molten material injected from the gate 74 does not directly hit (contact) the shaft 12 upon being ejected through the gate 74 of the runner 72 and melting of the shaft 12 is inhibited (i.e., the orientation helps prevent melting of the shaft 12).

In the injection step, the molten material is injected into the cavity 44 at a (relatively) high pressure and a (relatively) high speed. In other molds, the gate is disposed closer to the proximal side than the proximal end of the shaft (see, for example, Japanese Patent Application Publication No. 10-180802 disclosing ejecting molten material at a position proximal to the proximal end of the shaft). Accordingly, once the molten material is injected into the cavity in these other molds, the pressure of the molten material acts to push the shaft in the distal direction (distally). The shaft may thus move in the distal direction with respect to the support rod. In the case of the shaft movement, the length of the shaft exposed from the hub fluctuates.

In contrast, the manufacturing apparatus 40 according to the present embodiment positions the gate 74 (flowing portion 76) closer to the distal side than the proximal end 12*b* of the shaft 12 (i.e., the gate 74 is distal to the proximal end 12*b* of the shaft 12). Accordingly, the pressure of the molten material injected from the gate 74 actively flows in the proximal direction, and a relative movement of the shaft 12 with respect to the support rod 60 can be prevented. Especially, the gate 74 is provided at a distal side position by a margin of approximately 1 mm to 3 mm as compared with the proximal end 12*b* of the shaft 12 (i.e., the gate 74 is distal to the proximal end 12*b* of the shaft 12 by approximately 1 mm to 3 mm). Thus, the pressure of the molten material is uniformly dispersed in the cavity 44 and the molten material is capable of evenly flowing from the second space 52 to the first space 50. Accordingly, the molten material injected from the gate 74 smoothly fills the cavity 44 without moving the shaft 12.

The molten material injected in the injection step coagulates in the mold 42. The molten material is thus molded into the shape of the hub 14 in a state of adhesion to the shaft 12 (molding step: Step S5). As a result, the molded catheter with an integrated shaft 12 and hub 14 is formed.

A mold opening step is performed (Step S6) after the molding step. In the mold opening step, the first molding die 42*a* is moved relative to the second molding die 42*b* to open the mold 42. Then, the insert-molded catheter is taken out. Further, the distal end 12*a* of the shaft 12 is inserted into the communication hole of the strain relief 16 having the communication hole from the distal end to the proximal end and the strain relief 16 is moved toward the hub side (i.e., moved proximally) to be engaged with the attached portion 28 of the hub 14. The catheter 10 is completed as a result.

As illustrated in FIG. 1A, a gate trace 32 appears exactly at the position that corresponds to the gate 74 where the molten material was injected (plane of one wing 22) in the hub 14 of the catheter 10 manufactured by the manufacturing method described above. When viewed on the axis of the shaft 12, the gate trace 32 is positioned closer to the distal side (that is, between the distal end 12*a* and the proximal end 12*b* of the shaft 12) than the proximal end 12*b* of the shaft 12.

Figure 5A:
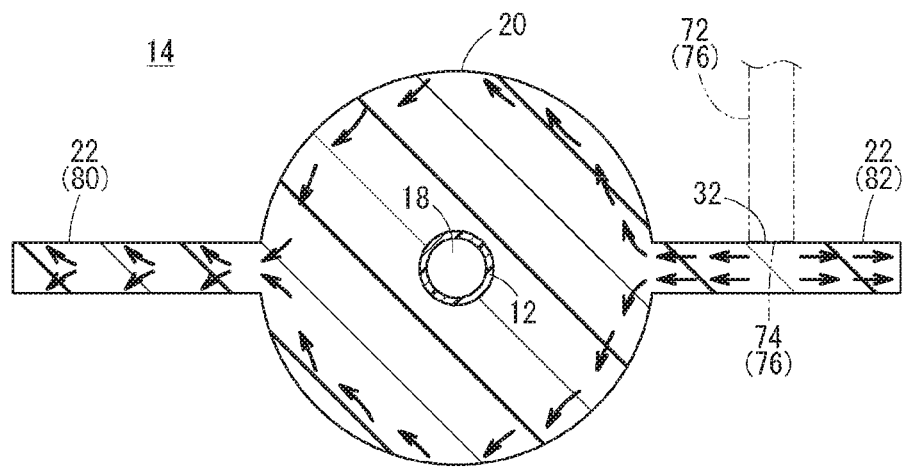
FIG. 5A is a cross-sectional view taken along line VA-VA of FIG. 1A.

As illustrated in FIG. 5A, residual stress (residual strain) is generated during the injection molding at the casting wall (surface part) of the molding material constituting the hub 14 in cross-sectional view orthogonal to the axial direction of the hub 14 in the place where the gate trace 32 is provided. The residual stress of the hub 14 can be measured by known measuring means (such as a polarization measuring device and an X-ray stress measuring device) after the manufacturing.

Specifically, the residual stress of one of the pair of wings 22 that lacked the gate 74 of the mold 42 and the residual stress of the other of the wings 22 that had the gate 74 are asymmetric (differ from each other) with the central axis of the shaft 12 serving as the base point of line symmetry as shown in FIG. 5A. In other words, the wing 22 that lacked the gate 74 has a first state 80 in which the residual stress is directed to the protruding end portion side (i.e., directed outwards in both the Y axis and Z axis directions as shown by the arrows in FIG. 5A), and the other wing 22 that had the gate 74 has a second state 82 in which the residual stress is directed so as to be separated from the gate 74 (i.e., directed outwards relative to the gate in the Y axis direction). Especially, the residual stress of the other wing 22 that had the gate 74 increases as cooling slows as compared with the casting wall of the other hub 14. In addition, as described above, the gate trace 32 may be formed as part of the second state 82 of the other wing 22.

Figure 5B:
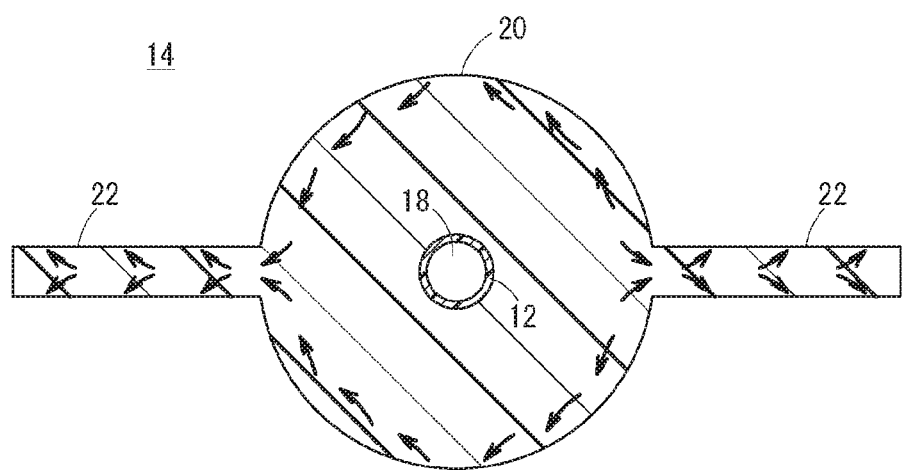
FIG. 5B is a cross-sectional view taken along line VB-VB of FIG. 1A.

With respect to the casting wall of the hub 14 at the predetermined position that had the gate 74, the casting wall of the hub 14 at the position shifted in the axial direction of the hub 14 from the predetermined position illustrated in FIG. 5B is (relatively) small in residual stress difference (generally has residual stress of line symmetry) even when the hub main body 20 and the pair of wings 22 have the same state. In addition, at a position away from the gate 74 where the molten material is injected, the residual stress is equalized during the coagulation as the dispersed molten material flows smoothly in the cavity 44, and thus the residual stress also decreases as compared with the position of the gate 74.

Accordingly, the position of the gate 74 can be confirmed, even in a state where the gate 74 has disappeared, by post-manufacturing measurement of the residual stress of the casting wall of the hub 14 molded by insert molding as described above. In the hub 14 manufactured by the manufacturing method described above, the place with an asymmetric and large residual stress indicates the position where the gate 74 was present during the measurement, and this position is present between the distal end 12*a* and the proximal end 12*b* of the shaft 12.

The method for manufacturing the catheter 10 and the catheter 10 according to the first embodiment have the following effects.

The method for manufacturing the catheter 10 helps make it possible to deter (prevent) the shaft 12 from moving during insert molding by positioning the shaft 12 such that the gate 74 is between the distal end 12*a* and the proximal end 12*b* of the shaft 12 in the disposition step. In other words, although the molding material is injected from the gate 74 and reaches a high pressure during molding material injection, the injected molding material actively flows in the proximal direction from the gate 74. Accordingly, the force pushing the shaft 12 in the distal direction is significantly reduced, and the hub 14 can be molded with the shaft 12 maintained at a predetermined position in the cavity 44. As a result, the quality of the catheter 10 manufactured by this manufacturing method is significantly enhanced, and manufacturing yield improvement and the like can be achieved.

In the hub 14 of the catheter 10 manufactured by this manufacturing method, a large residual stress is generated at the casting wall where the gate 74 was positioned during the insert molding. In other words, it can be verified that the gate 74 was positioned between the distal end 12*a* and the proximal end 12*b* of the shaft 12 when the residual stress at a predetermined position between the distal end 12*a* and the proximal end 12*b* of the shaft 12 exceeds the residual stress at a position shifted in the axial direction of the hub 14 from the predetermined position. Accordingly, the catheter 10 has high quality as movement of the shaft 12 is inhibited during the insertion molding and the hub 14 is tightly fixed to the shaft 12 in the desired position.

As a result, the catheter 10 is of relatively high quality with the shaft 12 that has a desired length. Accordingly, by using the catheter 10, users can perform treatment, examination, and the like in a satisfactory manner.

In the disposition step, the extending direction of the runner 72 and the extending direction of the shaft 12 have twisted positions (i.e., are askew relative to one another). Accordingly, it is possible to help prevent the molding material injected from the gate 74 from going straight to and directly hitting the shaft 12 during molding material injection. Accordingly, melting of the shaft 12 during injection can be effectively reduced, and the quality of the catheter 10 is further enhanced.

According to the manufacturing method, the shaft 12 is disposed along the axis of the first space 50, and thus it is possible to satisfactorily mold the hub main body 20 fixed to the shaft 12. In addition, operability improvement can be achieved for users since the molded hub 14 is provided with the wing 22.

According to the manufacturing method, the extending direction of the runner 72 intersects with the second space 52. Therefore, the molding material flowing through the runner 72 is injected into the second space 52 and hits (first contacts) the inner wall of the cavity 44. The molding material injected as a result flows in both the distal direction and the proximal direction from the second space 52 (while suppressing melting and the like of the shaft 12) to quickly fill the inside of the cavity 44. Disposition for perpendicular intersection is preferable. In other words, it is preferable that the runner has a longitudinal axis that is orthogonal to the axis of the shaft 12.

The manufactured catheter 10 has the first state 80 (residual stress) at a predetermined position of the hub 14 and the second state 82 (residual stress) different from the first state 80 opposite the first state 80 in the transverse direction of the hub 14 as shown in FIG. 5A. Thus, the position of the gate 74 during insert molding can be confirmed with greater ease.

The position of the gate 74 during insert molding of the catheter 10 can be confirmed even more easily based on the presence of the gate trace 32 at the predetermined position of the hub 14.

In the catheter 10, the pair of wings 22 differ from each other in terms of residual stress magnitude and direction. Thus, it is possible to confirm that the gate 74 was positioned at one of the wings 22 during insert molding. In addition, the hub 14 may be formed to have a sloped shape with the thickness of the distal end of the hub main body 20 smaller than the thickness of the proximal end, and thus force transmission is easy without slipping even when the hub 14 is pinched with fingers.

It should be noted that the catheter manufacturing method and manufactured catheter are not limited to the above-described embodiment and various modifications are possible in accordance with the gist of the invention. For example, the hub 14 of the catheter 10 can have any designed shape. For example, the catheter 10 may have a hub that lacks the pair of wings 22 (hub constituted by the hub main body 20 alone). As illustrated in FIG. 3, even in this case, it is possible to perform insert molding by positioning the gate 74 of the mold 42 between the distal end 12a and the proximal end 12b of the shaft 12. Further, in the manufacturing apparatus 40, the flowing portion 76 (the runner 72 and the gate 74) can be disposed at a position twisted with respect to the extending direction of the shaft 12 even in the hub 14 constituted by the hub main body 20 alone.

In another example, the hub 14 is capable of having a configuration in which another port is integrally molded in the hub main body 20. The gate 74 may be positioned in, for example, a space forming that port so that the flowing portion 76 (the runner 72 and the gate 74) is disposed at a position twisted with respect to the extending direction of the shaft 12.

As indicated by the two-dot chain line in FIG. 1B, the catheter 10 may have a shape in which a shaft 13 exposed from the hub 14 is curved in one direction between the distal end 12a and the proximal end 12b. The shaft 13 can be configured to be curved in one direction in, for example, at least half or more of the entire axial length (between the distal end 12a and the proximal end 12b) although the shaft 13 in FIG. 1B is curved only in the vicinity of the distal end 12a.

With respect to the shaft 13 configured as described above, the gate trace 32 (see FIG. 1A) formed in the hub 14 is capable of functioning as a marker indicating the curvature direction of the shaft 13. In other words, in FIG. 1B, the gate trace 32 (marker) is disposed on the same side as the outside of the curvature of the shaft 13 with respect to the central axis of the shaft 13. The catheter 10 configured as described above have improved usability for users. The reason is because a user can satisfactorily recognize the curvature direction of the shaft 13 by confirming the gate trace 32 of the hand-side hub 14 even when the shaft 13 is inserted in a patient's body.

It should be noted that the marker that indicates the curvature direction of the shaft 13 is not limited to the gate trace 32. Alternatively, a concave portion or the like may be formed by cutting of the gate trace 32. Additionally, integral molding of a suitable shape (concave portion, convex portion) may be performed during molding of the hub 14. Alternatively, the marker may be provided in the hub 14 by means of different processing (such as laser processing and printing).

The gate trace 32 (marker) may be disposed on the same side as the inside of the curvature of the shaft 13 with respect to the central axis of the shaft 13. In other words, the shaft may be curved in the direction that is opposite to the curvature direction of the shaft 13 in FIG. 1B (upward direction in the drawing). If a user is already aware of the relationship between the presence or absence of the marker and the curvature direction of the shaft 13, the user can understand the curvature direction of the shaft 13 by visually recognizing the hub 14 even when the shaft 13 is inserted in the body.

Second Embodiment

Next, a method for manufacturing a catheter 10A and the catheter 10A manufactured by the manufacturing method according to a second embodiment will be described. In the following description, the same reference numerals are given to the elements that have the same configurations or functions as in the above-described embodiment, and detailed description thereof will be omitted.

As illustrated in FIGS. 6A to 6C, a manufacturing apparatus 40A for the catheter 10A according to the second embodiment differs from the manufacturing apparatus 40 according to the first embodiment in that pins 90 protruding toward the axial center portion of a cavity 44A are provided on the inner wall constituting the cavity 44A of a mold 42A. A pin 90 is provided on each of the first and second molding dies 42a and 42b (so that there are two pins in total). The pins 90 face each other and are positioned closer to the distal side than the proximal end 12b of the shaft 12 disposed in the axial center portion of the cavity 44A (i.e., the pins 90 are distal to the proximal end 12b of the shaft 12). For example, the pin 90 may be provided at distal to the proximal end 12b of the shaft 12 by a distance of approximately 1 mm to 3 mm. The pin 90 may be disposed at a position overlapping the gate 74 of the mold 42A when viewed on the axis of the shaft 12.

The pin 90 of the second molding die 42b comes into contact with the shaft 12 and supports the shaft 12 in the disposition step when the shaft 12 is disposed in the cavity 44A (when the shaft 12 is first placed in a recess of the second molding die 42b). Likewise, the pin 90 of the first molding die 42a comes into contact with the shaft 12 as the mold clamping step is implemented and sandwiches the shaft 12 in cooperation with the pin 90 of the second molding die 42b. As a result, each pin 90 presses the shaft 12 in the mold-clamped state, and thus it is possible to further enhance the quality of the catheter 10 by helping to effectively prevent movement of the shaft 12 during molding material injection from the gate 74. It should be noted that only one pin 90 may be provided on the inner wall of the mold 42A (such as the second molding die 42b). The single pin 90 is capable of pressing the shaft 12 in cooperation with the support rod 60. In addition, three or more pins 90 may be provided in the mold 42A. The first molding die 42a and the second molding die 42b may differ from each other in terms of the number of pins.

Figure 7A:
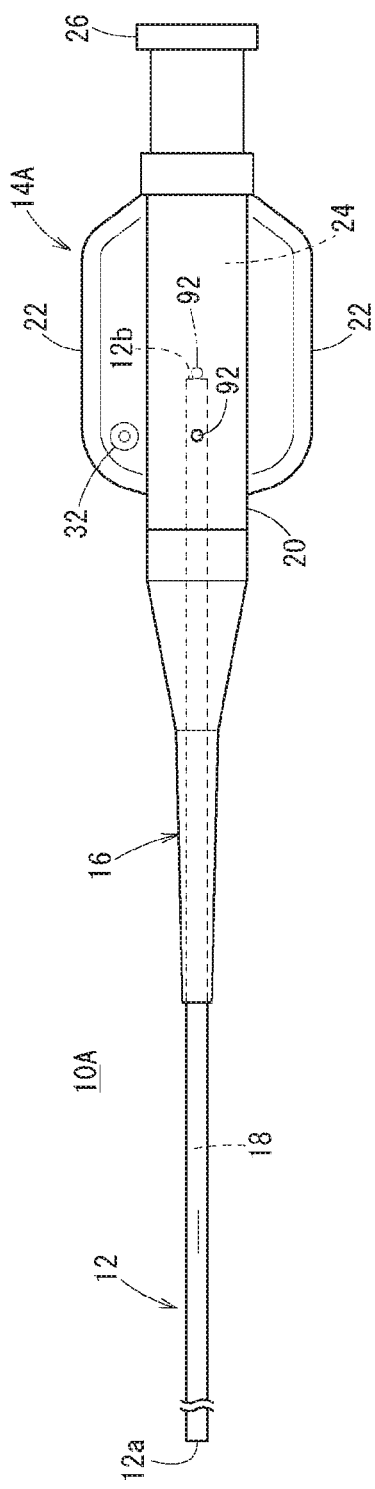
FIG. 7A is a partial plan view illustrating the proximal side of a catheter manufactured by the manufacturing apparatus in FIG. 6A.
Figure 7B:
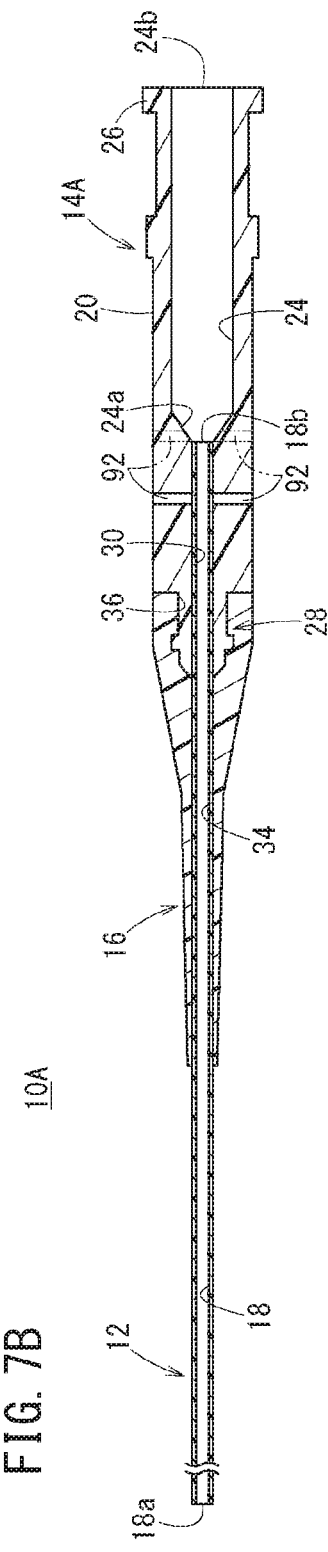
FIG. 7B is a lateral cross-sectional view of the catheter in FIG. 7A.

As illustrated in FIGS. 7A and 7B, a hub 14A manufactured by the manufacturing apparatus 40A has a concave portion 92 formed at a position corresponding to the pin 90 provided in the cavity 44A. The concave portion 92 is a through-hole that reaches the shaft outer surface from the outer peripheral surface of the molded hub 14A and functions as a window through which the shaft 12 in the hub 14A can be confirmed. In other words, a user can recognize that the shaft 12 has not moved in the distal direction by visually looking through the concave portion 92. If the shaft 12 cannot be seen through the concave portion 92, the user will know that the shaft 12 has moved in the distal direction, i.e., molding of the catheter 10A is imperfect.

As illustrated in FIGS. 8A and 8B, a manufacturing apparatus 40B according to a modification example of the second embodiment may be provided with the pins 90 that support the shaft 12 with respect to a mold 42B in an advanceable and retractable manner. For example, the pins 90 protrude toward the axial center of a cavity 44B and press the shaft 12 in the injection step. As a result, movement of the shaft 12 is inhibited during molten material injection, and the concave portion 92 is formed in the side surface of the hub 14A.

A withdrawal step is performed (see Step S6α in FIG. 4) after the molding step and before the mold opening step. In the withdrawal step, each of the plurality of pins 90 is retracted (withdrawn) from the cavity 44B to the inner wall of the mold 42B. As a result of this withdrawal step, the pins 90 can be smoothly pulled out from the concave portion 92 of the hub 14A before opening of the mold 42B. By subsequently carrying out the mold opening step, it is possible to release the molded hub 14A with relative ease from the cavity 44B.

Figure 4:
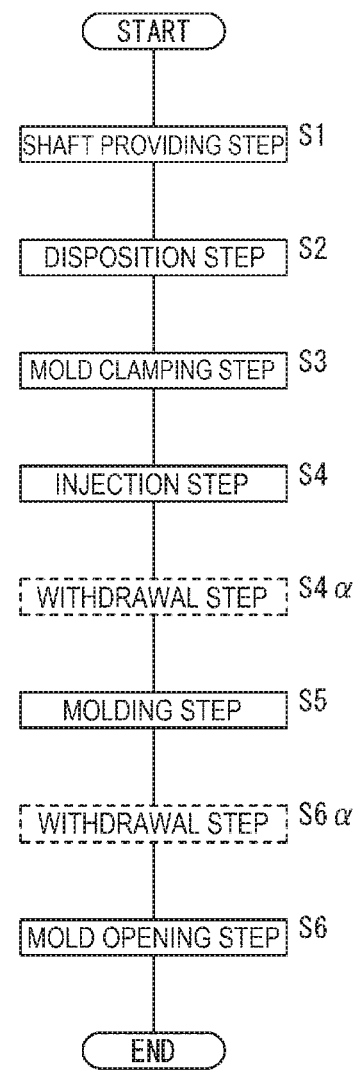
FIG. 4 is a flowchart illustrating a catheter manufacturing method.

When the pin 90 is advanceable and retractable, the retraction timing (withdrawal step) of the pin 90 may be carried out during molten material injection as illustrated in Step S4α in FIG. 4. In other words, a configuration (shape illustrated in FIGS. 1A and 1B) is possible in which the molten material flows into the position where the pin 90 was present and the concave portion 92 is not formed in the hub 14 by the pin 90 pressing the shaft 12 in the early stage of the molten material injection and the pin 90 being retracted at an appropriate timing during the molten material injection.

In another modification example, the mold 42A may be provided with a plurality of pins 90 that line up along the axial direction of the shaft 12 as indicated by the two-dot chain line in FIG. 6C. These aligned pins 90 can be disposed proximal to the proximal end 12b of the shaft 12 in part. As a result, a plurality of the concave portions 92 are created along the axial direction in the insert-molded hub 14A (see the two-dot chain lines in FIGS. 7A and 7B). Accordingly, when the shaft 12 is visually recognized via the proximal-side concave portion 92 that did not support the shaft 12, for example, it can be recognized that the shaft 12 has moved in the proximal direction, i.e., imperfect molding has occurred.

The concave portion 92 provided in the hub 14A (i.e., formed by the pin 90 of the mold 42A) is not particularly limited in terms of number (any number of concave portions 92 can be formed) and position. That is, the concave portion 92 is capable of adopting various configurations. For example, the pin 90 may be configured to protrude diagonally or horizontally with respect to the partition surface of the mold 42A, and the first molding die 42a and the second molding die 42b (both surfaces of the hub 14A) may differ from each other in terms of the number of pins.

The detailed description above describes a catheter manufacturing method and catheter manufactured by the catheter manufacturing method. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A catheter manufacturing method comprising:
positioning a shaft in a cavity of a mold, the shaft being an elongated tubular body having a lumen formed therein and configured to be inserted into a living body, the mold comprising a first mold die and a second mold die, the first and second mold dies contacting one another to define a closed space which is the cavity between the first and second mold dies, the shaft extending from a proximal end to a distal end in an axial direction and having a transverse direction perpendicular to the axial direction, the shaft possessing an outer surface and a center at a midpoint of the shaft in the transverse direction;
injecting a molding material into the cavity from a gate positioned between the proximal end and the distal end of the shaft in the axial direction, the position being offset from the center of the shaft in the transverse direction; and
molding a hub onto the shaft by solidifying the injected molding material in the cavity onto the outer surface of the shaft.

2. The catheter manufacturing method according to claim 1, wherein
the mold has a runner directing the molding material to flow from outside the cavity toward the gate, the runner possessing a longitudinal axis, and
the positioning of the shaft in the cavity of the mold such that the axial direction of the shaft has is offset and orthogonal with respect to the longitudinal axis of the runner.

3. The catheter manufacturing method according to claim 2, wherein
the hub comprises a tubular hub main body and a wing protruding outward from an outer peripheral surface of the hub main body,
the cavity comprises a first space for molding the hub main body and a second space for molding the wing, the second space having a longitudinal axis, and
the shaft is positioned to be parallel to the longitudinal axis of the second space.

4. The catheter manufacturing method according to claim 3, wherein the longitudinal axis of the runner intersects with the second space such that the molding material is injected directly into the second space.

5. The catheter manufacturing method according to claim 1, comprising:
the positioning of the shaft in the cavity of the mold being performed by positioning the shaft in a recess of either the first mold die or the second mold die and moving the first and second mold dies relative to one another to clamp the mold to define the closed space, and
pressing the shaft using at least one pin while the mold is clamped.

6. The catheter manufacturing method according to claim 5, wherein a concave portion is formed in the hub by the pin after the injecting of the molding material and the molding of the hub.

7. The catheter manufacturing method according to claim 5, wherein the at least one pin is a plurality of the pins that are arranged side by side along the axial direction of the shaft.

8. The catheter manufacturing method according to claim 5, comprising: withdrawing the pin from the cavity after the molding of the hub onto the shaft; and opening the mold after the withdrawing of the pin from the cavity.

* * * * *